United States Patent [19]

Rogers et al.

[11] 3,997,793
[45] Dec. 14, 1976

[54] APPARATUS AND METHOD FOR LOCATING AND QUANTIFYING OR DIRECTING A SOURCE OF IONIZING RADIATION

[75] Inventors: William Leslie Rogers, Ann Arbor; Michael A. Wainstock, Detroit, both of Mich.

[73] Assignee: University of Michigan, Ann Arbor, Mich.

[22] Filed: Nov. 7, 1975

[21] Appl. No.: 630,046

[52] U.S. Cl. .............................................. 250/491
[51] Int. Cl.[2] ........................................ G01N 21/00
[58] Field of Search ............... 250/491, 336, 363 S, 250/445 T

[56] References Cited
UNITED STATES PATENTS 3,861,807   1/1975   Le Screnier ................... 250/491 X

*Primary Examiner*—Davis L. Willis
*Attorney, Agent, or Firm*—Harness, Dickey & Pierce

[57] ABSTRACT

An apparatus and method for locating or directing a source of ionizing radiation such as X-rays, gamma rays, alpha particles, beta particles, etc. The preferred embodiment detects and locates abnormalities of the body such as ocular melanomas by detecting the emission of radiation from a melanoma which has absorbed a radioactive medium. The apparatus includes an ultrasound probe which emits ultrasonic waves along a first axis and detects a returned portion of the waves. The ultrasound probe is associated with a display which displays the returned portion of the waves in the time domain so that suspected abnormalities can be located. The ultrasound probe is used to guide a directional probe for detecting and quantifying ionizing radiation which is equipped with a focusing collimator having a focal point along a second axis. The two probes are supported so that the first and second axes converge at the focal point of the collimator. A range marker is associated with the ultrasonic detector which indicates the point of convergence of the axes on the ultrasonic display permitting guidance of the radiation detecting probe to the suspected abnormality.

32 Claims, 13 Drawing Figures

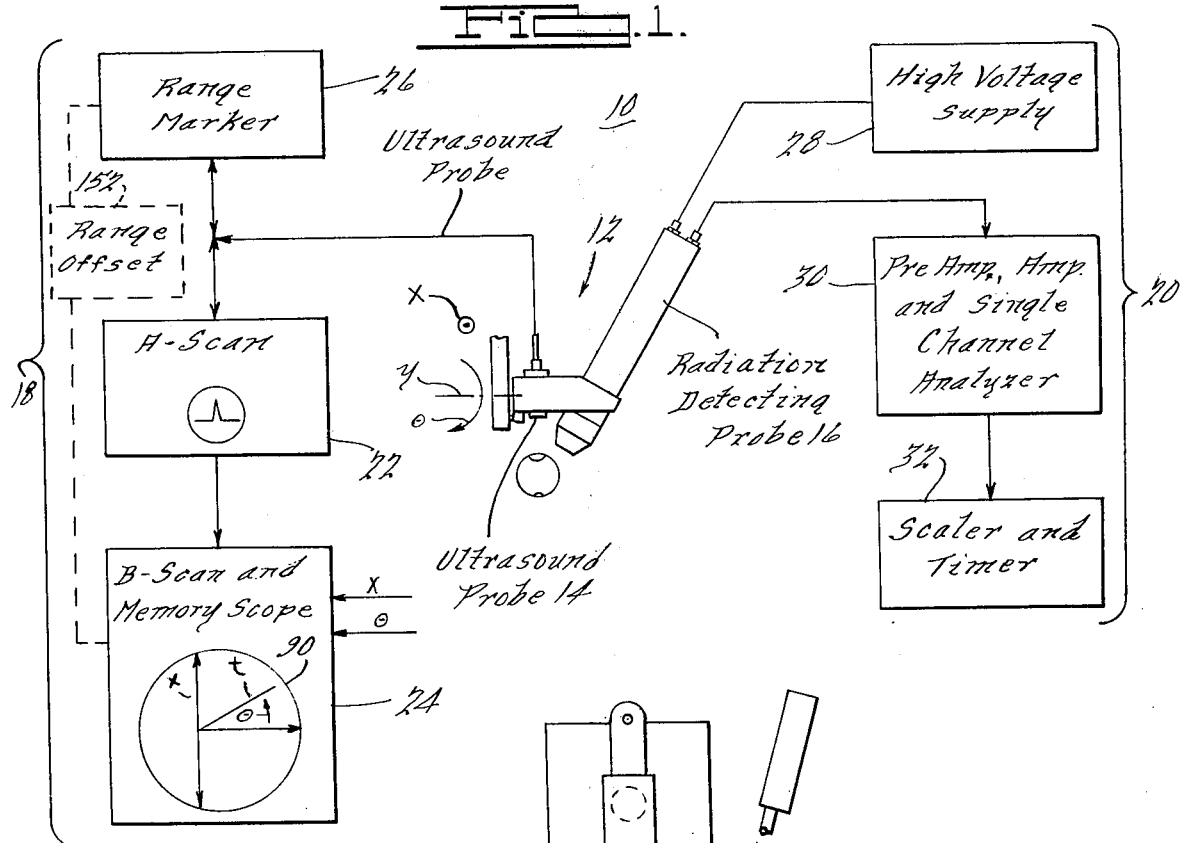
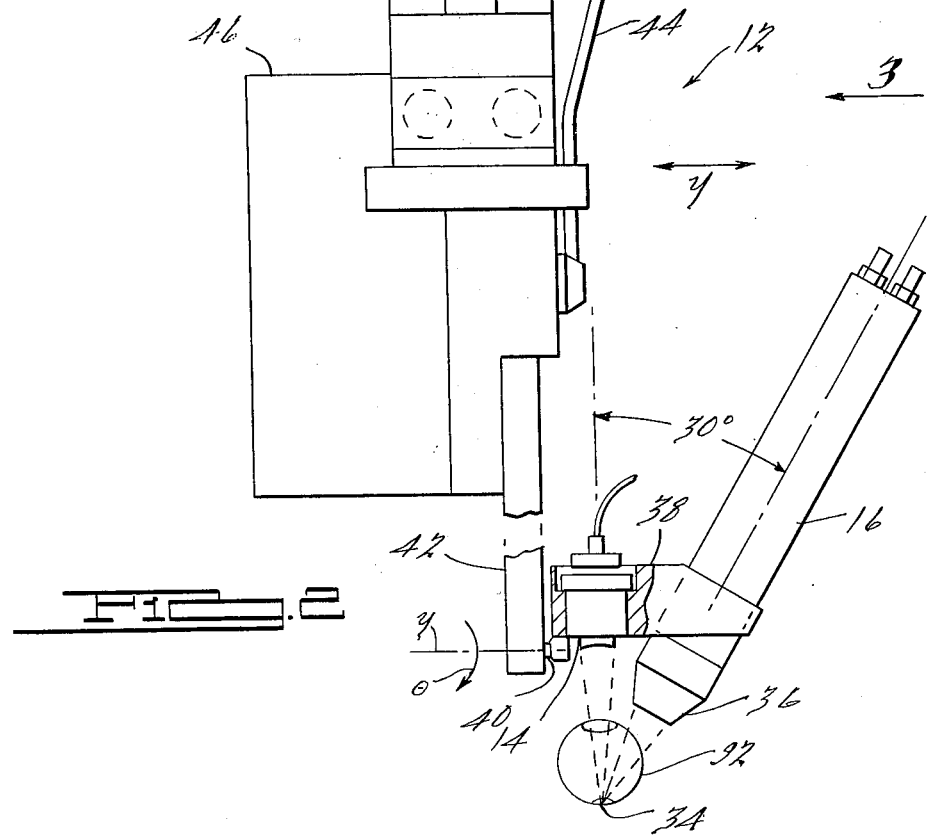

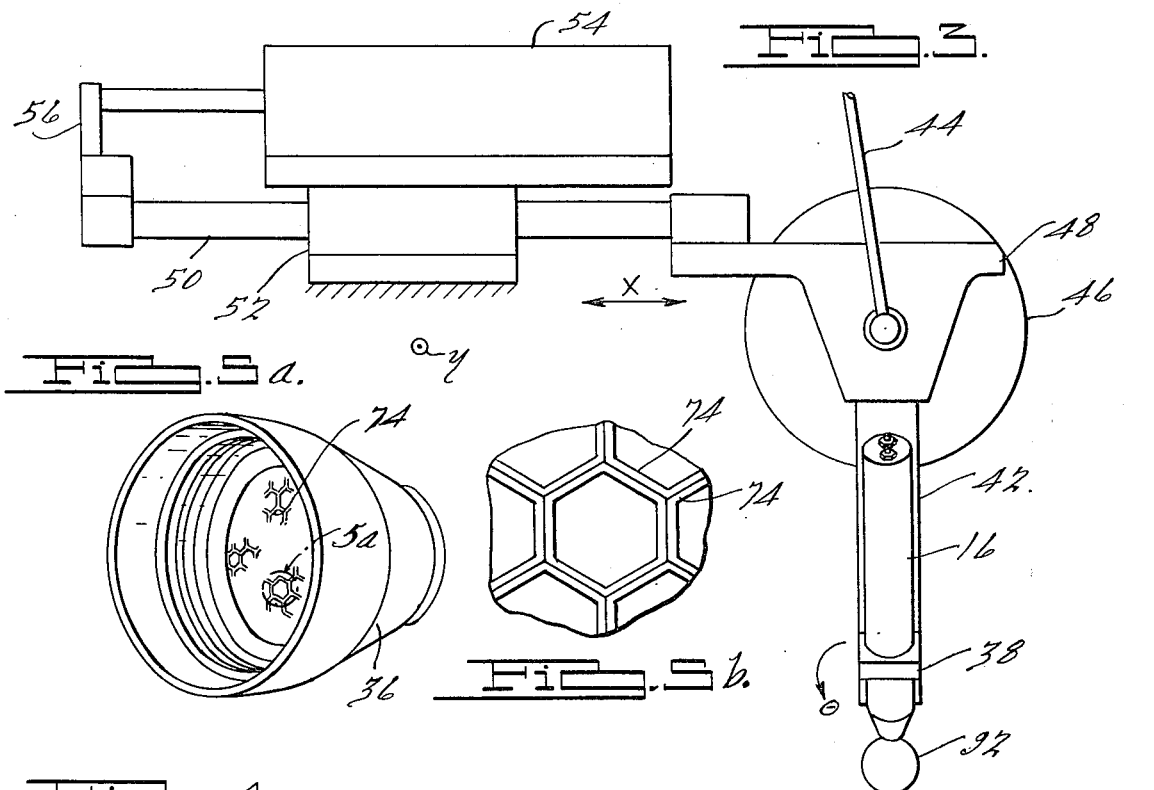
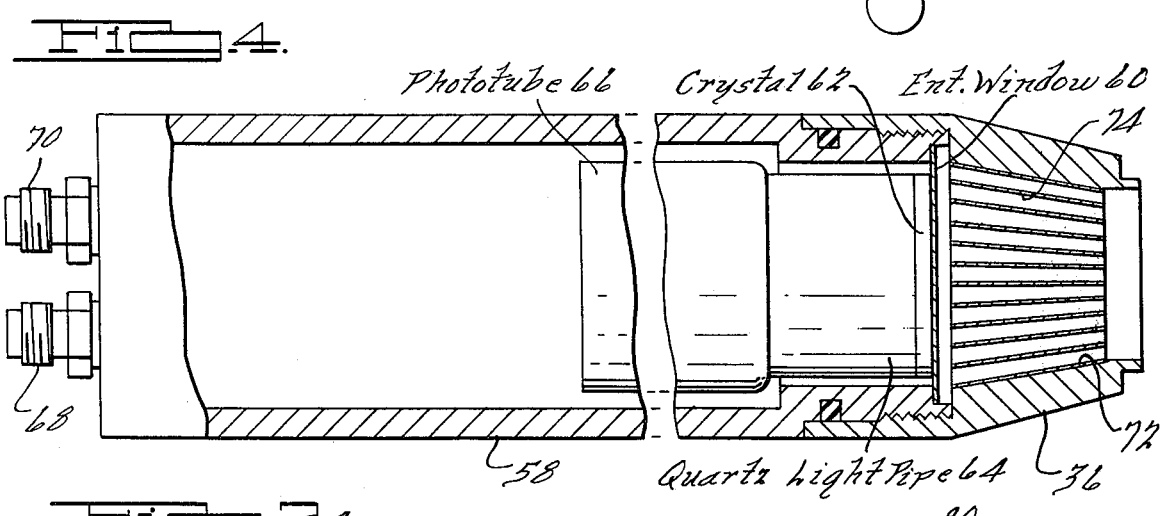
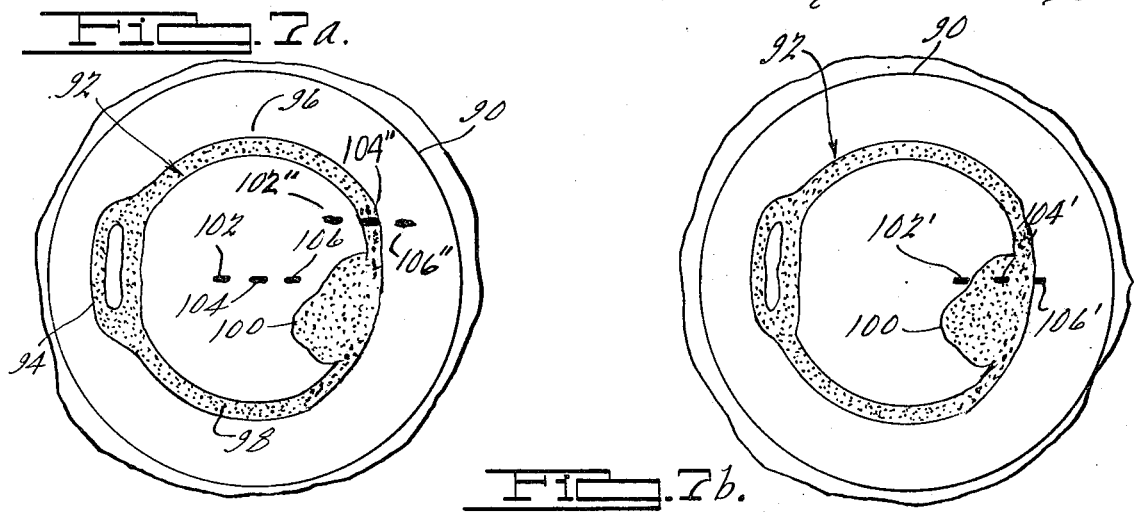

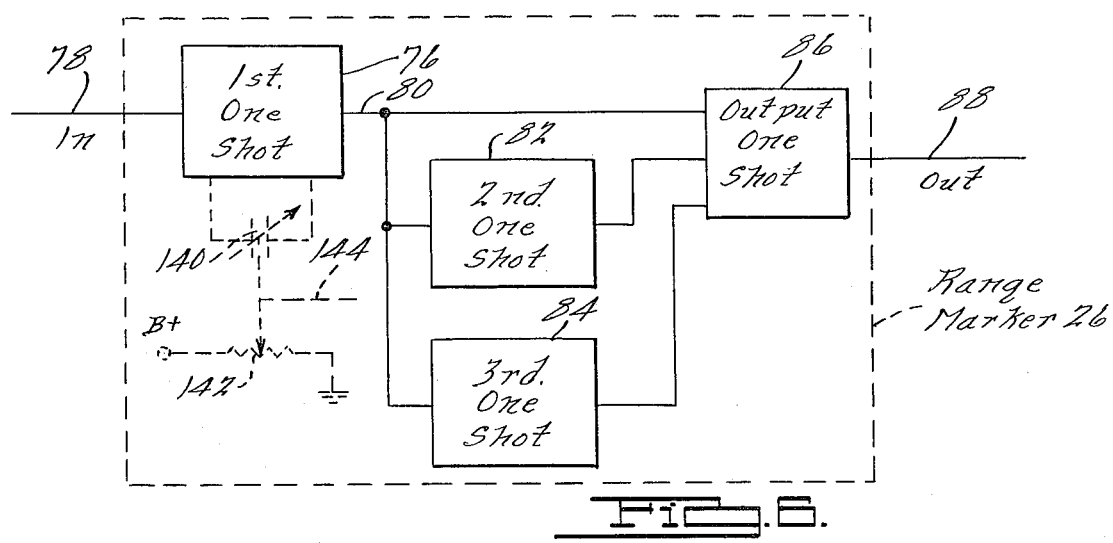
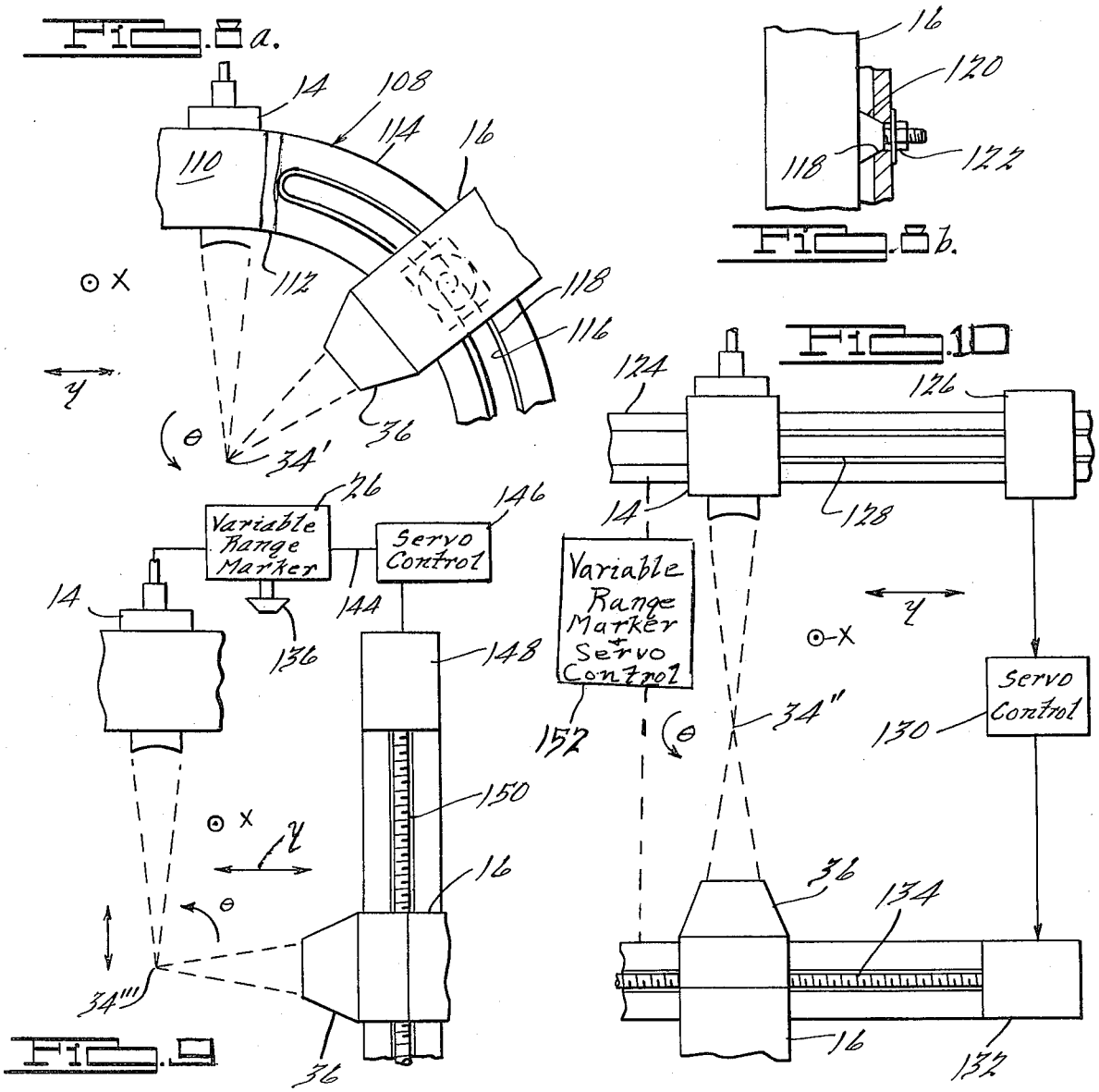

APPARATUS AND METHOD FOR LOCATING AND QUANTIFYING OR DIRECTING A SOURCE OF IONIZING RADIATION

BACKGROUND AND SUMMARY OF THE INVENTION

It has been discovered by others that an isotope of iodine, i.e., $^{125}I$, may be tagged on to the chloroquine so that, upon introduction to the human body, the chloroquine is absorbed into the body tissue with the $^{125}I$ label intact. It has also been discovered by others that the chloroquine is absorbed at a greater rate in melanotic tumors such as active melanomas of the eye. Accordingly, the type of absorbed abnormality, i.e., malignant melanoma versus hemangioma or other benign condition can be determined by measuring the concentration of chloroquine. Since the concentration of chloroquine is related to the presence of the associated isotope of iodine, an ionizing radiation detector which measures the ionizing radiation emitted by the isotope of iodine, and hence the concentration of the isotope of iodine and chloroquine, serves as an indication of the type of observed anatomical abnormality.

It has also been discovered by others that an ultrasound chart or "picture" of a body portion such as the eye can be constructed using an ultrasound probe by emitting ultrasound energy along a defined axis and displaying the returned portion of the ultrasonic energy in the time domain. Abnormalities in the body or other abrupt changes in the body structure causes the return of a portion of ultrasonic energy so that a display of the returned ultrasonic energy in the time domain portrays the location of these changes or abnormalities along the defined axis. By movement of the defined axis through a portion of the body, either by translational displacement or rotational displacement, an ultrasound chart or picture of that body portion can be displayed.

The present invention combines the two aforedescribed technologies in a unique way which permits accurate three-dimensional location of a radiation detecting probe with respect to the abnormality by guiding the radiation detecting probe using an ultrasound probe and an ultrasound signal display system. The advantages of the present inventon will be best appreciated if prior methods and apparatus for detecting abnormalities using a radiation detecting probe are considered.

One prior art method for determining the existence of an ocular melanoma is to introduce the isotope carrying chloroquine to the body so that it may be absorbed by the tissue in each eye of the patent. An uncollimated radiation detector measures the radiation emitted by each eye of the patient, for example, by counting the emission of ionizing radiation. The count differential between the respective eyes is used as an indication and measure of any abnormality. However, the standard deviation between two normal eyes, i.e., eyes which have no abnormalities, is substantial thereby leading to inconclusive results, particularly in the case of smaller tumors. Furthermore, the radiation is detected over a background level radiation emitted by the entire chloroquine absorbing tissue. The background radiation can readily mask small tumors thereby further reducing the sensitivity of this prior art method. The sensitivity of this prior art method is also reduced by variations in the probe placement.

Another prior art method of detecting ocular melanomas involves a surgical procedure in which the conjunctiva is incised, the eye rotated in its socket, and thereafter, the radiation detecting probe is accurately placed directly over the suspected tumor by a surgeon. Positioning is accomplished by visual means. In addition to this prior art method's drawback of requiring a surgical procedure, this prior art method still has the disadvantage of the above described method in that a substantial level of background radiation exists which masks the radiation from the area of interest. Furthermore, opaque eyes add additional complications in visual aiming of the detector.

Accurate positioning of a radiation detection probe relative to various anatomical features is useful for organs other than the eye and for radio-labelled compounds other than the chloroquine. Here, prior art methods for positioning may also include knowledge of anatomy and/or palpation or even sequential positioning (scanning) over whole areas of the body.

The present invention overcomes the disadvantages of the prior art methods and apparatus for locating sources of ionizing radiation, such as body abnormalities, by providing a radiation detector which has maximum responsiveness or sensitivity to radiation emitted from a restricted small volume in combination with an ultrasound guidance system for accurately placing the small volume of greatest sensitivity of the radiation detecting probe at a suspected abnormality. More specifically, the radiation detecting probe is provided with a focusing collimator which generally restricts the sensitivity of the probe to a small defined volume and is guided by an ultrasound probe so that the restricted volume may be located at a suspected abnormality. The ultrasound guidance system includes an ultrasound probe which emits a focused beam of ultrasonic energy along a first axis which coincides with the focal point of the collimator. The ultrasound guidance system further includes a signal processing system which detects and displays in the time domain any portion of the outgoing ultrasonic energy which is returned to the ultrasound probe. Ultrasonic energy is returned to the ultrasound probe when it strikes a body portion or substance of differing acoustic transmission. One such portion of different acoustic transmission would be a body abnormality such as a tumor, e.g., an ocular melanoma. By sweeping or displacing the ultrasound probe through an area of the body, and simultaneously or subsequently displaying the returned ultrasonic energy in the time domain, a chart or pattern can be constructed which indicates the location of portions of differing acoustic transmission. This display or indication can be used as a preliminary indicator of a suspected abnormality.

The collimated radiation detector is positioned relative to the ultrasound probe so that the focal point of the detector collimator will coincide, or substantially coincide, with either the focal point or the focal axis of the ultrasound probe. Preferably, the ultrasound display system is provided with a range marker which indicates on the display the location of the coincidence of the focal point of the radiation detecting probe and the axis of the ultrasound probe on the ultrasound display. By this means, the radiation detecting probe can be moved so that the focal point of its collimator is positioned at the suspected abnormality. Once it is so positioned, a radiation count of the emissions from the suspected abnormality can be made. After that radiation count is made, the radiation detecting probe can be moved to locate the focal point of its collimator in normal tissue so that a background or reference radiation count can be made. The difference in the radiation counts is an indication of specificity of the abnormality for the uptake of the particular radio-labelled compound employed.

The range marking system may provide a plurality or range marks. For example, three range marks can be generated, a first at the coincidence of the focal point of the radiation detecting probe collimator and the axis of the ultrasound probe, a second space a predetermined distance from the coincidence mark along either the axis of the ultrasound probe or, if the configuration is such that the axis of the radiation detecting probe lies in the plane of the ultrasound imagine, i.e., the x-theta plane (described hereinafter), the axis of the radiation detecting probe, and a third also spaced a predetermined distance from the coincidence mark along either the axis of the ultrasound probe or the axis of the radiation detecting probe, but on the opposite side of the coincidence mark.

In the preferred embodiment, the range marker system includes a timer which is activated upon emission of the ultrasonic pulse by the ultrasound probe and introduces a substantial pulse simulating a returned ultrasonic pulse at a time corresponding to the return time of a pulse reflecting from the coincidence point. In the embodiment providing two additional range marks, two additional pulses are provided, one occurring at the return time of a pulse reflecting from a predetermined distance short of the coincidence point, and another occuring at the return time of a pulse reflecting from a predetermined distance on the opposite side of the coincidence point.

In view of the above discussion, and the detailed description of the preferred embodiment hereinafter, it will be appreciated that the present invention provides a means for accurately locating and measuring the emissions from a source of radiation such as a body abnormality. The apparatus of this invention is believed to increase the percentage of positive detection of abnormalities relative to either the ultrasound or the radiation detecting methods of the prior art. Moreover, a surgical procedure is not required. Other advantages and novel features will be apparent in view of the following detailed description of the preferred embodiment.

BRIEF DESCRIPTION OF THE DRAWINGS

FIG. 1 is a block diagram of an apparatus for locating a source of ionizing radiation;

FIG. 2 is a first view of a dual probe assembly of the apparatus of FIG. 1;

FIG. 3 is a second view of a dual probe assembly of FIG. 1 taken in the direction of Arrow 3 of FIG. 2;

FIG. 4 is a view, partly in cross section, of a radiation detecting probe of the apparatus of FIG. 1;

FIGS. 5a and 5b are illustrations of a collimator of the radiation detecting probe of FIG. 4;

FIG. 6 is a block diagram of a range marker of the apparatus of FIG. 1;

FIGS. 7a and 7b are illustrations of a display provided by the apparatus of FIG. 1;

FIGS. 8a and 8b are views of another embodiment of the present invention;

FIG. 9 is a view of yet another embodiment of the present invention; and

FIG. 10 is a view of still another embodiment of the present invention.

DETAILED DESCRIPTION OF THE PREFERRED EMBODIMENT

In FIG. 1, an apparatus 10 according to the present invention for locating a source of ionizing radiation is illustrated in block form. The apparatus 10 includes a dual probe assembly 12 comprising an ultrasound probe 14 and a radiation detecting probe 16, to be described in detail with respect to FIGS. 2 and 3, an ultrasound system 18, and a radiation counting system 20. The ultrasound system 18 includes an A-scan system 22 for generating electrical pulses which are provided to the ultrasound probe 14 to cause the emission of ultrasound pulses from the ultrasound probe 14 and for detecting electrical pulses received from the ultrasound probe 14 representative of returned ultrasonic pulses detected by the ultrasound probe 14. The ultrasound system 18 further includes a B-scan and memory scope system 24 which displays in the space domain ultrasound pulses which are returned to the ultrasound probe 14 in the time domain. More specifically, the ultrasound probe 14, with the radiation detecting probe 16, may be rotated about the $y$ axis (located in the plane of the drawing and horizontally disposed with respect to the apparatus as shown) through an angle $\theta$, hereinafter theta, and may be moved along the $x$ axis (perpendicular to the plane of the drawing). The display of the memory scope 24 reflects the $x$ displacement and angle of rotation theta as illustrated in the drawing. The returned ultrasonic pulses are displayed in a time domain (as illustrated on the memory scope 24 by the t axis) with pulses returning at a later point in time being displaced to the right with respect to the illustration in the drawing. The t axis represents radial displacement from the origin lying on the axis $x$ in the direction theta.

The ultrasound system 18 further includes a range marker 26 which detects the emission of an electrical pulse from the A-scan system 22 and returns an electrical pulse to the A-scan 22 at predetermined time intervals after the emission of the pulse by the A-scan 22. The returned electrical pulses represent predetermined distances along the axis of the ultrasound probe 14.

The radiation detecting system 20 includes a high voltage supply 28 for the radiation detecting probe 16, a preamplifier, amp, and single channel analyser 30 which receives pulses from the radiation detecting probe 16 representing received ionizing radiation and provides representative output pulses when said received pulses meet certain amplitude criteria and a scaler and timer 32 which receives and counts the output pulses from the preamplifier, amp and single channel analyser 30.

The A-scan 22, the B-scan and memory scope 24, the high voltage supply 28, the preamplifier, amp and single channel analyzer 30 and the scaler and timer 32 may be commercially acquired as follows:

| Component | Model No. | Supplier |
|---|---|---|
| A-scan | | Sonometrics Systems, Inc. New York, New York |
| B-scan and memory scope 24 | | Sonometrics Systems, Inc. |
| High voltage supply 28 | 3002 | Canberra Industries 45 Gracey Avenue Meriden, Conn. 06450 |
| Preamplifier, amp and single | | |

-continued

| Component | Model No. | Supplier |
|---|---|---|
| channel analyser 30 | 818 | Canberra Industries |
| Scaler and timer 32 | 1491 | Canberra Industries |

In FIG. 2 the probe apparatus 12 is illustrated in greater detail. The axis of the ultrasound probe 14 is seen to be oriented vertically while the axis of the radiation detecting probe 16 is seen to lie in the same plane as the axis of the ultrasound probe 14, but inclined at an angle of 30 degress with respect to same. The inclination of the ultrasound probe 14 and the radiation detecting probe 16 and the orientation of the plane containing the two probes 14 and 16 about the axis of the ultrasound probe 14 is arbitrarily chosen except for the condition that their respective axes coincide, or substantially coincide. The ultrasound probe 14 emits ultrasonic energy along its axis and includes known means for focusing the ultrasound probe at a point 34. The radiation detecting probe 16 includes a collimator 36 which has a focal point at 34. Accordingly, the focal point of the ultrasound probe 14 and the collimator 36 of the radiation detecting probe 16 coincide. As will be apparent in view of the later discussion herein, it is not necessary that the focal point of the collimator 36 of the radiation detecting probe 16 coincide with the focal point of the ultrasound probe 14. Rather, other embodiments can be constructed in which the focal point of the collimator 36 of the radiation detecting probe 16 is located at, or substantially at, the axis of radiation of ultrasonic energy of the ultrasound probe 14.

The ultrasound probe 14 and the radiation detecting probe 16 are mounted with the coincidence of the focal point of the collimator 36 of the radiation detecting probe 16 and the focal point of the ultrasound probe 14 by means of a bracket member 38 which engages and supports the ultrasound probe 14 and the radiation detecting probe 16. The bracket 38 is attached to a rotatable member 40 which is secured to an arm 42. The rotatable member 40 is adapted to be rotatively driven about an axis $y$, through an angle of rotation theta. The arm 42 is mounted for translational displacement in the $x$ direction, i.e., in the direction which is perpendicular to the plane of the drawing, as will be explained in connection with FIG. 3.

The arm 42 contains a chain drive (not shown) which connects the rotatable shaft 40 to a rotatable lever 44 so that movement of the lever 44 causes rotation of the shaft 40, and hence, rotation of the ultrasound probe 14 and the radiation detecting probe 16. The degree of rotation, i.e., the angle theta, is translated into an electrical signal by a rotary potentiometer 46 which is connected to the lever 44.

With reference now to FIG. 3, the radiation detecting probe 16, the bracket 38, the arm 42, the handle 44, and the rotary potentiometer 46 can be seen. The arm 42 along with probes 14 and 16 are mounted on a support member 48 which in turn is displaceable in the $x$ direction by means of a slide arrangement comprising slide shaft 50 and bearing 52. The degree of $x$ displacement is translated into an electrical signal by a linear potentiometer 54 which is connected to the slide shaft by a linkage 56 as shown. The potentiometers 46 and 54 are commercially available units. The electrical rotational and translational displacement signals from the rotary potentiometer 46 and the linear potentiometer 54 are provided to the B-scan and memory scope 24 as will be understood by those skilled in this art.

With reference now to FIG. 4, the radiation detector 16 is shown in greater detail. The radiation detector 16 generally comprises a commercially available ionizing radiation detector, often referred to as a scintillation detector, which is illustrated generally at 58 in combination with a specially adapted collimator 36. The detector 58 is commercially available from the Harshaw Chemical Co., Solon, Ohio and includes an entrance window 60, and a crystal 62 for converting alpha particles, beta particles, gamma rays or X-rays into visible light. The visible light from the crystal 62 is transmitted by a quartz light pipe 64 to a phototube 66. The phototube 66 converts the visible light to electrical pulses. The detector 58 is energized by a high voltage supply 28 which is connected to one terminal 68 and provides electrical output pulses from the phototube 66 on a second terminal 70.

The collimator 36 is threaded to the detector 58 and includes a conical concentric bore 72 which is defined by lines which converge at the focal point of the collimator 36. A plurality of converging hexagonal tubes 74 of silver sheet stock reside in the conical bore 72 of the collimator 36.

With reference now to FIGS. 5a and 5b, the assembly of hexagonal tubes 74 can be seen in better detail. Each converging hexagonal tube abuts an adjacent hexagonal tube at respective ones of its six sides as shown in FIG. 5b. FIG. 5a omits the illustration of the abutment between the tubes. The overall effect is a honeycomb-like structure as is apparent from the drawings.

Each of the hexagonal tubes 74 is formed by wrapping silver sheet stock about a converging hexagonal pin. The converging pin is designed so that the sides of the hexagonal tubes are defined by lines which converge upon the focal point 34 of the collimator 36 so that the internal surfaces of the hexagonal tubes 74 converge at the focal point 34 of the collimator 36.

With reference now to FIG. 6, the range marker 26 is shown in greater detail. The range marker essentially comprises four one-shot multivibrators as illustrated. A first one-shot multivibrator 76 receives the outgoing pulse from the A-scan 22 on line 78 and provides a delayed output pulse on line 80 to each of the second one-shot multivibrator 82, the third one-shot multivibrator 84, and an output oneshot multivibrator 86. The first one-shot multivibrator output pulse on line 80 is provided a predetermined period after receipt of the pulse on line 78, for example, $6.66 \times 10^{-5}$ sec. after receipt of the pulse on line 78. The provision of the delayed pulse on line 80 immediately results in the generation of an output pulse on output line 88 by the output one-shot multivibrator 86. The second one-shot multivibrator 82 receives the delayed pulse on line 80 and provides an output pulse to the output one-shot multivibrator 86 a predetermined time after the receipt of delayed output pulse on line 80, for example $0.68 \times 10^{-5}$ sec. after the receipt of the delayed output pulse on line 80. The output one-shot multivibrator pulse 86 provides another output pulse on line 88 upon receipt of the output from the second one-shot multivibrator 82 which will be appreciated as being generated $7.34 \times 10^{-5}$ sec. after the receipt of the arrival of the pulse on line 78. The third one-shot multivibrator 84 receives the delayed pulse on output line 80 and provides an output pulse to the output one-shot multivibrator 86 $1.34 \times 10^{-5}$ sec. after the receipt of the delayed pulse on line 80. The output one-shot multivibrator 86 provides a third output pulse on line 88 which appears $8.0 \times 10^{-5}$ sec. after the arrival of the pulse on line 78. The output one-shot multivibrator provides its three output pulses on line 88 which is connected to the A-scan 22 so that the three output pulses from the output one-shot multivibrator 86 simulates three very strong returns of ultrasound energy to the A-scan 22.

With reference now to FIGS. 7a and 7b, the appearance of the returned ultrasound signals on the memory scope 90 of the B-scan and memory scope unit 24 is illustrated. Some liberties have been taken in the portrayal of the appearance of the returned ultrasound signals for the sake of clarity. The portrayals of FIGS. 7a and 7b represent the ultrasound picture of a human eye which can be seen on the scope detector 90 generally at 92. The portrayal 92 illustrates the position of the iris of the eye at 94 and the rim of the eyeball at 96 and 98. A suspected melanoma appears at 100. The portrayals of FIGS. 7a and 7b are negatived in that the outline of the eye 92 and the melanoma 100 is shown dark against a white background, while in fact, the reverse is true.

In the portrayal of FIG. 7a three range marks are seen at 102, 104, and 106 which are generated by the range marker 26.

The point in time at which the three pulses 102–106 have been generated is selected in this embodiment so that the range mark 104 coincides with the location on the screen 90 of the focal point of the collimator 36 of the radiation detecting probe 16. This has been accomplished by determining the distance from the face of the ultrasound probe 14 to the point of coincidence 34 of the axis of the ultrasound probe 14 and the focal point of the collimator 36 of the radiation detecting probe 16 and setting the time of generation of the range mark 104 to be equal to the return time of a pulse from the point of coincidence 34. The time of generation of the range marks 102 and 106 have been set so that the range mark 102 is five millimeters nearer the probe than the range mark 104 and the range mark 106 is five millimeters further from the probe than the range mark 104. In the preferred embodiment, the point of coincidence 34 was 55 millimeters from the surface of the ultrasound probe 14, and therefore, the range mark 102 represents 50 millimeters from the radiating surface of the probe 14 and the range mark 106 represents 60 millimeters from the surface of the ultrasound probe 14.

In the use of the apparatus 10, after introduction of the isotope-carrying chloroquine to the body portion under investigation, the examining physician or technician will first align the ultrasound probe 14 so that it is directed to the area in which tumors are suspected. The image shown on the scope 90 is obtained through translation of the axis of generation of ultrasound waves by the probe 14 either by rotating the probe 14 by movement of the lever 44 so as to vary the angle theta in the $x$ direction or through linear movement of that axis in the $x$ direction by movement of the slide 50 in the $x$ direction of both. Once the image has been formed, any area of suspected abnormality, such as at 100, can be seen. The range marker 26 can be activated so as to display the three range marks 102–106.

The examining physician or technican, by observing the relative position of the range mark 104 and the suspected melanoma 100 can move the ultrasound probe 14, and consequently, identically move the radiation probe 16, so that the range mark 104 appears at the suspected abnormality 100. This may be accomplished by theta displacement of the ultrasound probe 14, $x$ displacement of the ultrasound probe 14, or $y$ displacement of the ultrasound probe 14 (by a slide not illustrated). The result of such movement is shown in FIG. 7b wherein the range marks have been shown as relocated to 102', 104' and 106'. Since the range mark 104' is now located in the image at the suspected melanoma, the examining physician or technican is assured that the focal point of the collimator 36 is also located at the suspected melanoma. Hence, the radiation detecting probe 16 has been accurately guided to the suspected melanoma 100 by use of the ultrasound probe 14.

With the collimator 36 of the radiation detecting probe 16 now positioned so that its focal point coincides with the suspected melanoma, a count of the radiation at the location 34 can be made. By virtue of the collimator 36, the response of the radiation detecting probe 16 is substantially limited to radiation emitted along the axes of the hexagonal tubes 74 of the collimator 36. Since the axes of the tubes 74 coincide at the focal point 34 of the collimator 36, the radiation detecting probe 16 is more responsive to radiation sources at the focal point 34 than at any other location. The radiation detecting probe 16 will also be responsive to other radiation sources generally within the fan-shaped volume or pair of cones defined by the converging lines of the collimator 36, however, to a lesser degree than to radiation sources at the focal point 34. Before or after the radiation count of the suspected melanoma 100 has been made with the probe positioned with the focal point 34 in front of the suspected melanoma 100, a second reading can be taken with the focal point 34 in apparently good tissue such as the location of the focal point 34 shown as location 104'' in FIG. 7a. The difference in the radiation counts when the probe is located at the suspected melanoma 100 and any adjacent apparently sound tissue, is an indication as to whether the observed abnormality is a melanoma or rather some benign condition. This method is believed to be a substantial advance over the prior art methods for determining whether the observed abnormality is a malignant melanoma either by ultrasound methods or radiation detecting methods.

In FIGS. 8a and 8b, and alternative embodiment of the present invention is illustrated. In the FIGURE, the previously described ultrasound probe 14 and the radiation detecting probe 16 having the collimator 36 is illustrated. In the embodiment of FIGS. 8a and 8b, the support 38 has been replaced with a support 108 which permits variable placement of the radiation detecting probe 16 relative to the ultrasound probe 14. The support 108 includes a portion 110 which secures the ultrasound portion 14, an angulated connecting portion 112 and an arcuate, slotted portion 114 on which the radiation probe 16 is slidably mounted. More specifically, the arcuate portion 114 includes a radial slot 116 having a center of curvature located at the point 34' of coincidence between the axes of the ultrasound probe 14 and the focal point of the collimator 36 of the radiation detecting probe 16. The slot 116 has a chamfered face 118 which is engaged by a conical securing member 120 which is frictionally secured to the chamfered face 18 by a securing or clamping means illustrated as a nut and screw arrangement at 122. A second arcuate member (not shown) having a corresponding arcuate slot 116 with a greater radius can be located to provide a second support for the radiation detecting probe 16 to aid in maintaining the alignment of the probe 16 with the focal point location 34.

In the embodiment of FIGS. 8a and 8b, the radiation detecting probe 16 may be moved relative to the ultrasound probe 14 without changing the point of coincidence 34' between the axis of the ultrasound probe 14 and the focal point of the radiation detecting probe 16. By means of the structure of FIGS. 8a and 8b, the examination of certain body parts can be facilitated.

In FIG. 9, another embodiment of the present invention is illustrated. In the figure, the previously described ultrasound probe 14 and radiation detecting probe 16 is illustrated. In the embodiment of FIG. 9, the ultrasound probe 14 is provided with a variable range marker 26 having a control 136 (shown in detail by dashed lines in FIG. 1) for adjusting the capacitance of a delay setting, variable capacitor 140 of the first one-shot multivibrator 76 of FIG. 6. By adjusting this variable capacitor 140, the period of delay of the first one-shot multivibrator 76 is varied to delay the occurrence of the three range marks (each to an equal degree) which are described in connection with FIGS. 6 and 7. As a result, the relative positions of the range marks are not changed with respect to each other, the range marks are moved along the axis of the ultrasound probe 14. Variation of the capacitor 140 also varies a mechanically-coupled potentiometer 142 so as to provide a signal on line 144 which represents the displacement of the range marks relative to the ultrasound probe 14. The signal on line 144 is provided to a servocontrol 146 which activates a motor 148 to cause rotation of a screw 150 which is threadedly engaged with a support for the radiation detecting probe 16. The servocontrol 146 is effective to control the motor 148 so that the radiation detecting probe 16 is moved in chronism with the movement of the range detector marks so that the focal point of the collimator 36 of the radiation detecting probe 16 is moved to coincide with the central range mark 104 generated by the second oneshot multivibrator 82. Note that the radiation detecting probe 16 is positioned relative to the axis of generation of ultrasound waves by the ultrasound probe 14 so that the focal point 34''' of the collimator 36 of the radiation detecting probe 16 will always be located on the axis of generation of ultrasonic waves by the ultrasound probe 14 regardless of the movement of the radiation detecting probe 16. However, the focal point 34''' may or may not be located at the focal point of the ultrasound probe 14. In fact, the focal point 34''' of the collimator 36 is displaced both nearer and more distant from the ultrasound probe 14 than the focal point of the ultrasound probe 14. Nonetheless, movement of the radiation detecting probe 16 maintains the focal point of the collimator 36 in coincidence with the central range mark 104 generated by the second one-shot multivibrator 82.

In FIG. 10, yet another embodiment of this invention is illustrated. In the embodiment of FIG. 10, the previously described ultrasound probe 14 and the radiation detecting probe 16 are positioned in opposed relationship with the axis of the collimator 36 of the radiation detecting probe 16 aligned with the axis of ultrasound transmission of the ultrasound probe 14. The ultrasound probe 14 may be moved manually along a slide 124. The movement of the ultrasound probe 14 is detected and converted into electrical signals by means of a linear potentiometer 126 which is connected to the ultrasound probe 14 by a shaft 128. The electrical signals representing the movement of the ultrasound probe 14 are provided to a servocontrol 130 which in turn provides control signals for a motor 132. The motor 132 turns a screw member 134 which is threadedly engaged with a support for the radiation detecting probe 16 so as to move the radiation detecting probe 16 in accordance with the rotation of the screw 134. The rotation of the screw member 134 is controlled by the servocontrol 130 so that the radiation detecting probe moves in synchronism with the ultrasound probe 14 and the axis of the collimator 36 of the radiation detecting probe 16 is maintained at 34''. Of course, the radiation detecting probe 16 may be moved manually and the apparatus 130, 132 and 134 may be connected to the ultrasound probe 14 to move it in synchronism with the radiation detecting probe 16 to achieve the same result. In addition, longitudinal motion of the radiation probe along its own axis may be similarly servocontrolled either by longitudinal motion of the ultrasound probe along its axis or by varying the time delay of the range marker in such a manner that the focal point of the radiation detector collimator is moved to coincide with the position of the range marker. Preferably, this is accomplished by providing the embodiment of FIG. 10 with a variable range marker and servocontrol 152 comprising components 26, 136 and 140–150 as described with respect to FIGS. 6 and 9 for moving the probes 14 and 16 toward and away from each other. Preferably, this is accomplished by a motor 148 and screw 150 arrangements which interconnects the parallel slides which carry the probes 14 and 16 so as to move the slides toward and away from each other while maintaining the parallel relationship of the slides. The variable range marker and servocontrol 152 is effective to alter the distance between the probes 14 and 16 so that the focal point of the collimator 36 continuously coincides with the movable central range mark 104.

In the embodiments of FIGS. 8–10, the ultrasound probe 14 and the radiation detecting probe 16 are provided with associated components 22–32 shown in FIG. 1 to provide an ultrasound display and a radiation count as described. Additionally, a support for the entire assemblies represented in FIGS. 8–10 is provided so that the probes 14 and 16 are movable together in the x direction, the y direction, and through angles theta as illustrated in FIGS. 2 and 3.

In the range marker system described in detail with respect to FIG. 6, the range marks are aligned with the axis of generation of ultrasonic waves by the ultrasound probe 14. In an embodiment in which the axis of the radiation detector is contained in the plane of the ultrasound image (x, theta) the range marks can also be aligned with the axis of the collimator 36 of the ultrasound detector 16 by displacing the location of the first and third range marks on the presentation appearing on the memory scope 90. This can be accomplished by providing a range offset control 152 illustrated by dash lines in FIG. 1 which is responsive to the generation of the first and third range marks and which adjusts the x displacement of the scope in one direction for the first range mark and in the opposite direction for the second range mark so that the range marks are located along the axes of the radiation detecting probe 16 on the display provided by the memory scope 90. In that manner, the range marks will indicate the orientation of the radiaton detecting probe 16 rather than the orientation of the ultrasound probe 14.

In view of the above description of the preferred embodiment of the subject invention, it will be appreciated that the physician is able to accurately locate a suspected tumor, position the focal point of a collimated radiation detector at the suspected tumor and attain a radiation count of the tumor. Importantly, a surgical procedure is not required. In the case of melanomas of the eye, this system has the further advantage in that a determination of background radiation can be made in sound tissue in the same eye thereby avoiding the usual variations between the eyes.

Although the present disclosure has been directed to the detection of ionizing radiation from a source within a body, this method can also be used to detect sources of ionizing radiation within other structures. Moreover, although this invention has been described as a method and apparatus for detecting a source of ionizing radiation, it can be readily adapted for guiding a source of ionizing radiation for radiation therapy. For example, the radiation detecting probe 16 can be replaced with an emitter of a beam of ionizing radiation. For the purposes of the description of this embodiment, the radiation detecting probe 16 should be considered as a radiation emitting probe 16 having a collimator 36 for collimating a beam of ionizing radiation. Using this method, a physician can guide the radiation emitting probe to a tumor or other area to be radiated, then activate the radiation emitting probe 16 for the requisite period. The collimator 36 concentrates the ionizing radiation on the tumor or other specified area.

While it will be apparent that the preferred embodiments of the invention disclosed are well calculated to fulfill the objects above stated, it will be appreciated that the invention is susceptible to modification, variation and change without departing from the proper scope or fair meaning of the invention.

What is claimed is:
1. An apparatus for detecting a source of radiation comprising:
   ultrasound means for emitting ultrasonic waves along a first predetermined axis and for receiving a returned portion of said ultrasonic waves along said first predetermined axis for providing a signal representing said returned portion of ultrasonic waves;
   signal processing means for said ultrasonic means output signal for identifying and locating a suspected source of radiation along said axis;
   radiation detecting means for detecting ionizing radiation along a second predetermined axis; and
   support means for supporting said ultrasound means and said radiation detecting means with a known relationship between said first and second predetermined axis so that said radiation detecting means can be guided to said suspected course of radiation by said ultrasound means.
2. An apparatus according to claim 1 with said support means supports said ultrasound means and said radiation detecting means with said first and second predetermined axes substantially coinciding at least at one location.
3. An apparatus according to claim 2 further including collimating means for collimating ionizing radiation received by said radiation detecting means so that said radiation detecting means has increased responsiveness to radiation at a restricted volume.
4. An apparatus according to claim 3 wherein said ultrasonic means includes means for identifying said location of coincidence.
5. An apparatus according to claim 2 wherein said signal processing means includes display means for displaying said returned portion of said ultrasonic waves.
6. An apparatus according to claim 5 wherein said display means displays said returned portion of said ultrasonic waves in the time domain.
7. An apparatus according to claim 6 wherein said ultrasound means includes displacing means for causing displacement of said first axis thereby providing a display of said returned portion of said ultrasonic waves.
8. An apparatus according to claim 7 wherein said displacing means provides rotational displacement of said predetermined axis of said ultrasound means.
9. An apparatus according to claim 8 wherein said displacing means provides translational displacement of said predetermined axis of said ultrasound means.
10. An apparatus according to claim 2 wherein said first predetermined axis and said second predetermined axis converge toward said location of coincidence.
11. An apparatus according to claim 2 wherein said first predetermined axis and said second predetermined axis are coextensive.
12. An apparatus according to claim 1 further includng collimating means for collimating ionizing radiation received by said radiation detecting means so that said radiation detecting means has increased responsiveness to radiation at a restricted volume.
13. An apparatus according to claim 12 wherein said ultrasonic means includes means for identifying said location of coincidence.
14. An apparatus according to claim 13 wherein said signal processing means includes display means for displaying said returned portion of said ultrasonic waves.
15. An apparatus according to claim 14 wherein said display means displays said returned portion of said ultrasonic waves in the time domain.
16. An apparatus according to claim 15 wherein said ultrasound means includes displacing means for causing displacement of said first axis thereby providing a display of said returned portion of said ultrasonic waves.
17. An apparatus according to claim 16 wherein said displacing means provides rotational displacement of said first predetermined axis.
18. An apparatus according to claim 17 wherein said displacing means provides translational displacement of said first predetermined axis.
19. An apparatus for detecting a radioactive abnormality comprising:
   ultrasound means including an ultrasound probe for emitting ultrasonic waves along a first predetermined axis and for receiving a returned portion of said ultrasonic waves along said first predetermined axis for providing a signal representative thereof;
   display means for displaying said signal as a function of time so that said returned portion of said ultrasonic waves is displayed in the time domain and indicates a suspected abnormality;

radiation detecting means including a radiation detecting probe for detecting ionizing radiation along a second predetermined axis;

quantifying means associated with said radiation detecting means for quantitatively determining the magnitude of ionizing radiation received along said second predetermined axis; and support means for supporting said ultrasound probe and said radiation detecting probe with said first and second predetermined axes substantially coinciding at least at one location and for providing cooperative displacement of both said ultrasound probe and said radiation detecting probe for locating said location of coincidence at said suspected abnormality.

20. An apparatus according to claim 19 further including a range marking means for generating indications on said display substantially indicative of said location of coincidence of said first and second predetermined axes to aid in placement of said location of coincidence at said suspected abnormality.

21. An apparatus according to claim 20 further including collimating means for collimating ionizing radiation received by said radiation detecting probe so that said radiation detecting probe has increased responsiveness to radiation at said point of coincidence.

22. An apparatus comprising:
ultrasound means for emitting ultrasonic waves along a first predetermined axis and for receiving a returned portion of said ultrasonic waves along said first predetermined axis for providing a signal representative thereof;

display means for displaying said signal as a function of time so that said returned portion of said ultrasonic waves is displayed in the time domain;

radiation means for detecting or emitting radiation along a second predetermined axis; and support means for supporting said ultrasound means and said radiation means with a known relationship between said first and second predetermined axes so to that said radiation means can be guided by said ultrasound means.

23. An apparatus according to claim 22 wherein said support means supports said ultrasound means and said radiation means with said first and second predetermined axes substantially coinciding at least at one location.

24. An apparatus according to claim 22 further including collimating means for collimating radiation emitted or detected by said radiation means so that said radiation means has increased response or effect at a restricted volume.

25. An apparatus according to claim 22 wherein said support means movably supports said ultrasound means relative to said radiation means with said known relationship between said first and second predetermined axes.

26. An apparatus according to claim 22 wherein said support means includes means for arcuately moving one of said ultrasound means and said radiation means while maintaining said known relationship between said first and second predetermined axes.

27. An apparatus according to claim 25 wherein said support means includes means for moving one of said radiation means and said ultrasound means in synchronism with the other of said radiation means and said ultrasound means.

28. An apparatus according to claim 27 wherein said support means supports said radiation means and said ultrasound means with said first and second predetermined axes at substantially 90° each relative to the other.

29. An apparatus according to claim 27 wherein said support means supports said ultrasound means and said radiation means with said first and second predetermined axes being coextensive.

30. An apparatus according to claim 29 wherein said support means supports said ultrasound means and said radiation means in opposed relationship.

31. A method comprising the steps of;
emitting ultrasonic waves along a first predetermined axis;

receiving a returned portion of said ultrasonic waves along said first predetermined axis;

displaying said returned portion of said ultrasonic waves in the time domain; and directing a radiation detector in accordance with said display returned portion of said ultrasonic waves.

32. A method comprising the steps of:
emitting ultrasonic waves along a first predetermined axis;

receiving a returned portion of said ultrasonic waves along said first predetermined axis;

displaying said returned portion of said ultrasonic waves in the time domain; and directing a radiation emitter in accordance with said displaying returned portion of said ultrasonic waves.

* * * * *